United States Patent [19]

Choperena et al.

[11] Patent Number: 4,754,186

[45] Date of Patent: Jun. 28, 1988

[54] DRIVE NETWORK FOR AN ULTRASONIC PROBE

[75] Inventors: Alfredo M. Choperena, Hockessin; Chhaya K. Kohli, Wilmington, both of Del.

[73] Assignee: E. I. Du Pont de Nemours and Company, Wilmington, Del.

[21] Appl. No.: 945,508

[22] Filed: Dec. 23, 1986

[51] Int. Cl.$^4$ ............................................. H01L 41/08
[52] U.S. Cl. .................................... 310/316; 318/116
[58] Field of Search ................................ 310/316–319; 73/961; 331/4, 116 R; 318/116, 118

[56] References Cited

U.S. PATENT DOCUMENTS

| | | | |
|---|---|---|---|
| 2,498,760 | 2/1950 | Kreithan | 250/36 |
| 2,738,172 | 3/1956 | Spiess, Jr. et al. | 259/1 |
| 2,752,512 | 6/1956 | Sarratt | 310/8.1 |
| 2,814,575 | 11/1957 | Lange, Jr. | 134/1 |
| 2,917,691 | 12/1959 | Prisco et al. | 318/118 |
| 3,246,516 | 4/1966 | Maropis | 73/290 |
| 3,266,311 | 8/1966 | Andreasen et al. | 73/290 |
| 3,381,525 | 5/1968 | Kartluke et al. | 73/67 |
| 3,394,274 | 7/1968 | Jacke et al. | 310/8.1 |
| 3,489,930 | 1/1970 | Shoh | 310/8.1 |
| 3,524,085 | 8/1970 | Shoh | 310/8.2 |
| 3,546,498 | 12/1970 | McMaster et al. | 310/8.2 |
| 3,629,726 | 12/1971 | Popescu | 331/116 M |
| 3,668,486 | 6/1972 | Silver | 318/116 |
| 3,694,713 | 9/1972 | Durén et al. | 318/116 |
| 3,727,112 | 4/1973 | Popescu | 317/146 |
| 3,827,023 | 7/1974 | Henriquez et al. | 340/10 |
| 3,906,120 | 9/1975 | Geating | 427/4 |
| 3,931,533 | 1/1976 | Raso et al. | 310/8.1 |
| 4,134,097 | 1/1979 | Cowles | 340/7 R |
| 4,169,984 | 10/1979 | Parisi | 310/323 |
| 4,175,242 | 11/1979 | Kleinschmidt | 310/316 |
| 4,275,363 | 6/1981 | Mishiro et al. | 331/4 |
| 4,277,710 | 7/1981 | Harwood et al. | 310/316 |
| 4,301,968 | 11/1981 | Berger et al. | 239/102 |
| 4,302,728 | 11/1981 | Nakamura | 331/25 |
| 4,329,875 | 5/1982 | Nolting et al. | 73/290 V |
| 4,341,116 | 7/1982 | Bilstad et al. | 73/290 V |
| 4,363,242 | 12/1982 | Heyman | 73/761 |
| 4,403,508 | 9/1983 | Langlois | 73/589 |
| 4,445,064 | 4/1984 | Bullis | 310/316 |
| 4,468,581 | 8/1984 | Okada et al. | 310/316 |
| 4,523,465 | 6/1985 | Fasching et al. | 73/290 V |
| 4,540,981 | 9/1985 | Lapetina | 340/618 |
| 4,562,413 | 12/1985 | Mishiro et al. | 331/116 R |
| 4,578,650 | 3/1986 | Watson | 331/160 |
| 4,587,958 | 5/1986 | Noguchi et al. | 310/316 X |
| 4,641,053 | 2/1987 | Takeda | 310/316 X |

OTHER PUBLICATIONS

Ultrasonics, vol. 5, Oct. 1967, pp. 214–218.
Brochure—Heat Systems Ultrasonics Inc., 1984.
Neppiras, E. A., "Motional Feedback Systems for Ultrasonic Transducers", 1971 Ultrason Conf. Papers, Surrey, England, pp. 56–58, IPC Science and Technology Press, 1971.
Bullis, David C. and Budak, Aram, "Response of Ultrasonic Reactive Loads", IEEE. Trans. on Sonics and Ultrasonics, vol. SU-24, No. 2, Mar. 1982.

Primary Examiner—Mark O. Budd

[57] ABSTRACT

A drive network for an ultrasonic probe includes a network operative to apply a pulse to a feedback terminal of a phase comparator substantially simultaneously with the application at the probe of an excitation signal from a source at a predetermined frequency. This insures that at the start-up of the drive network the frequency of the feedback signal to the phase comparator leads the excitation signal also being applied thereto, to cause the excitation signal from the source to increase toward the resonant frequency of the probe, thereby to search for the resonant frequency of the probe.

3 Claims, 2 Drawing Sheets

DRIVE NETWORK FOR AN ULTRASONIC PROBE

BACKGROUND OF THE INVENTION

1. Field of the Invention

The invention relates to a drive network for an ultrasonic probe and, in particular, to a drive network having an arrangement therein adapted to search for the resonant frequency of the probe in an efficient ordered manner.

2. Description of the Prior Art

Ultrasonic vibratory probes such as that sold by, among others, Heat Systems-Ultrasonics Inc., Farmingdale, N.Y. operate most efficiently when the frequency of the excitation energy applied to the probe is substantially equal to the resonant frequency of the probe. Once a probe is excited at its resonant frequency, however, variations in the probe or in the loading to which the probe is exposed will cause the resonant frequency of the system to change. Known in the art are various arrangements whereby the frequency of vibration of the probe is monitored during its operational cycle in order to continuously track the resonant frequency of the system of which the probe is a part so that maximum energy transfer may occur. Exemplary of such systems are those described in U.S. Pat. Nos. 4,468,581 (Okada et al.); 4,363,242 (Heyman); 4,302,728 (Nakamura); 4,277,710 (Harwood et al.); 4,175,242 (Kleinochmidt); 3,931,533 (Raso et al.); 4,578,650 (Watson); and German Patent No. 2,721,225 (Siemens).

Upon startup of the probe it is the usual practice to select an excitation frequency, couple the same to the probe and observe response thereof. U.S. Pat. No. 4,445,064 (Bullis), assigned to the assignee of the present invention, is an example of a system having limited tracking and no search capability. If the probe vibrates it is assumed that the selected excitation frequency is sufficiently close to the resonant frequency of the probe so that the transfer of energy can occur. However, such a mode of initiating the operation of the probe is not believed advantageous.

U.S. Pat. Nos. 4,562,413 and 4,275,363 (both Mishiro) disclose complex differential current arrangements whereby the resonant frequency of the probe may be systematically searched. Neither of these arrangements utilize a phase locked loop network in conducting the search for the resonant frequency.

As noted earlier, since the resonant frequency of the probe changes with use or after repair, it would be advantageous to provide an arrangement whereby, upon initiation of the operation of the probe, the resonant frequency thereof may be quickly and accurately established. Accordingly, in view of the foregoing, it is believed advantageous to provide a network operable on the initial excitation of the ultrasonic probe for efficiently seeking the resonant frequency of the system.

SUMMARY OF THE INVENTION

The present invention relates to a drive network for an ultrasonic probe having a predetermined resonant frequency associated therewith. The drive network includes a source of probe excitation signals operable at any one of a predetermined plurality of selectable frequencies in a predetermined frequency range. The excitation signals are applied to the probe through a motional bridge circuit which also serves to monitor the response of the probe to the excitation signals and to provide a feedback electrical signal representative thereof. A phase comparator controls the frequency of the excitation signals generated by the source by comparing the excitation signal applied at a first input terminal of the phase comparator to the feedback signal applied at the second input terminal thereof. At start-up, if the frequency of the feedback signal is greater than that of the excitation signal the phase comparator acts to increase the frequency of the excitation signal. Once start-up is achieved the phase comparator acts to increase the frequency of the excitation signal if the phase of the feedback signal is leading the excitation signal, or vice versa.

In accordance with the present invention a network is provided that is operable in response to an enable signal generated by a controller and occurring just prior to the initial application of an excitation signal of an initial frequency to the probe to inject a pulse at the second input terminal of the phase comparator. By so doing the signal present at the feedback input terminal of the phase comparator has a frequency greater than that of the excitation signal so that the frequency of the excitation begins to increase progressively from the initial starting frequency until the resonant frequency of the probe is encountered.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
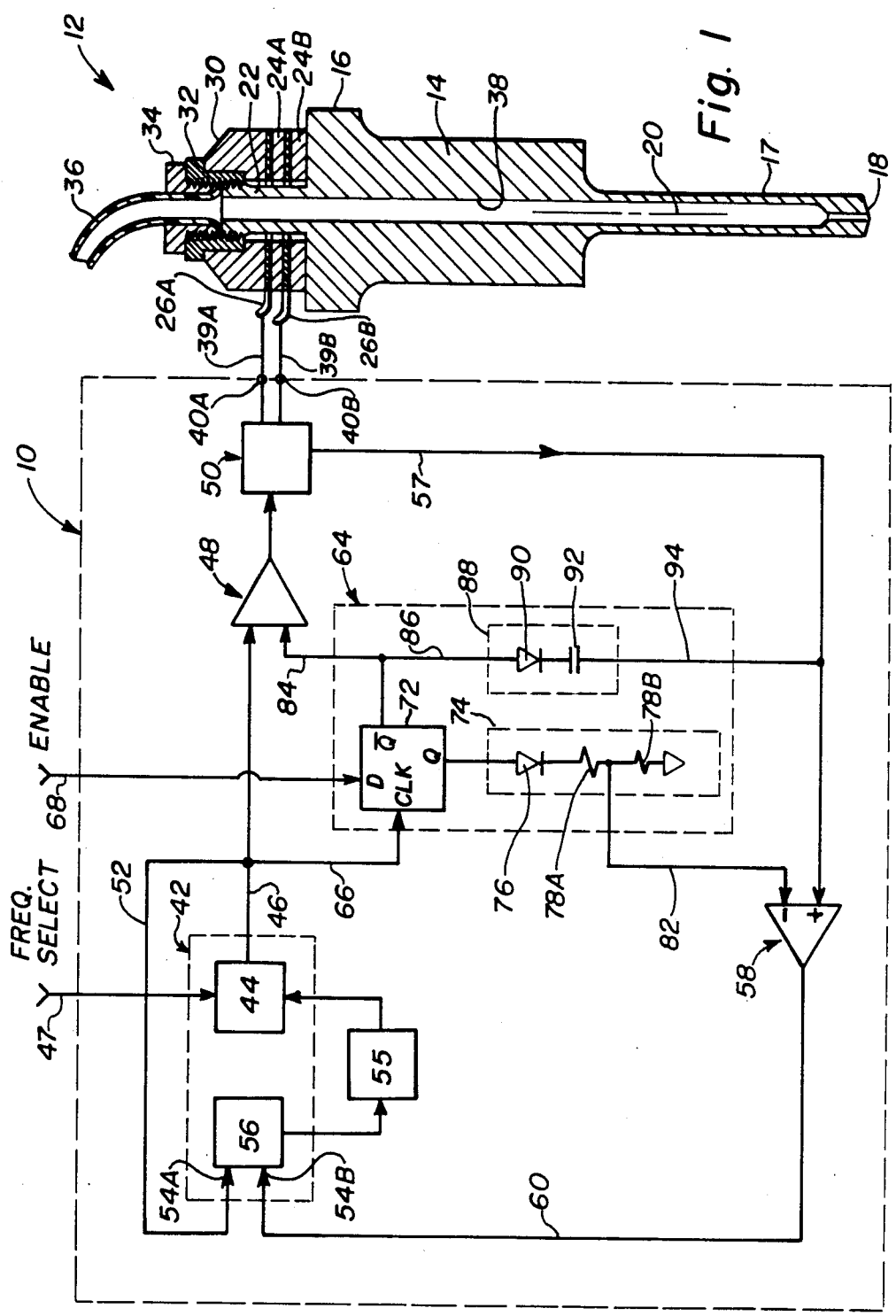
FIG. 1 is a highly stylized schematic and pictorial representation of an ultrasonic probe and the drive network for the probe in accordance with the present invention.

Throughout the following detailed description similar reference numerals refer to similar elements in all figures of the drawings.

The present invention relates to a drive network generally indicated by reference character 10 used to apply excitation energy to an ultrasonic horn, or probe, generally indicated by reference character 12. The probe 12 is an axially elongated member having a body portion 14 extending from an enlarged head portion 16 through a needle-like portion 17 to a beveled tip 18. The probe 12 has an axis 20 therein. An axially projecting threaded boss 22 extends from the head 16. A pair of piezoelectric crystals 24A, 24B, each having an associated electrodes 26A and 26B, respectively, is received on the boss 22.

The crystals 24A and 24B are held in place by a backpiece 30. A nut 32 threads onto the boss 22 to clamp together the above described assembly. A tubing connector 34 threads onto the nut 32 and a tube 36 is interconnectable with the connector 34.

A bore 38 extends centrally and axially through the probe 12. In operation the tube 36 is connected to suitable aspirating and hydrating sources whereby hydrating liquid can be aspirated by and dispensed from the probe 12. In addition, the probe 12 provides sonic energy which serves to dissolve a tabletted material disposed in the vessel into which the hydrating liquid is dispensed.

The electrodes 26A and 26B from the crystals 24 are connected over respective leads 39A and 39B to the respective output terminals 40A and 40B of the drive network 10. The drive network 10 includes a phase locked loop arrangement 42 having a voltage controlled oscillator 44 therein. The oscillator 44 is operative to produce a probe excitation signal on an output line 46 at any selected one of a predetermined plurality of frequencies in a predetermined continuous frequency range. The initial frequency is selected via an input line 47. The excitation signal on the output line 46 of the oscillator 44 is applied to the probe 12 first through a suitable power amplifier 48 and then through a motional bridge network 50. Suitable for use as the amplifier 48 is a push-pull power integrated circuit sold by Lambda under model number 8500. Details of the bridge 50 are disclosed in the articles by Neppiras, "Motional Feedback Systems For Ultrasonic Transducers", 1971 Ultrason. Conf. Papers, Surrey, England, pp. 56–58, IPC Science and Technology Press, 1971 and Bullis and Budak, "Response of Ultrasonic Motional Bridge Circuits Under Resistive and Reactive Loads", IEEE. Trans. on Sonics and Ultrasonics, Vol. SU-24, No. 2, March 1982.

The excitation signal from the oscillator 44 is applied over a line 52 to the first input terminal 54A of a phase comparator 56 that forms part of the phase locked loop 42. The output of the phase comparator 56 is applied via a low pass filter 55 to drive the oscillator 44.

The motional bridge 50 serves to generate electrical signals representative of the motion of the probe 12. These feedback signals are applied over a line 57 to a suitable level detector network 58. The output of the level detector network 58 is applied over a line 60 to the second input terminal 54B of the phase comparator 56. The level detector network 58 serves to compare the magnitude of the feedback signal on the line 57 to a predetermined threshold and thus insures that the level of the signal applied on the line 57 exceeds a predetermined threshold. As will become clearer herein the threshold voltage applied to the inverting terminal of the level detector network 58 is initially held to some relatively high level $V_i$ (FIG. 2) to keep the phase locked loop arrangement 42 from tracking noise on the line 57 prior to enablement. The output signal on the line 46 thus remains at some predetermined selected initial frequency $f_s$ prior to the occurrence of an ENABLE signal. Suitable for use as the level detector network 58 is a device sold by National Semiconductor under model number 311.

Suitable for use as the phase locked loop arrangement 42 is a device manufactured and sold by RCA under model number CD4046. The phase comparator 56 in this device used in the present invention is an edge-controlled digital memory network acting on the positive edges of the signals on the input lines 54A and 54B. At start-up (immediately subsequent to the ENABLE signal) if the frequency of the feedback signal on the line 54B is greater than the frequency of the signal on the line 54A the oscillator 44 is driven to output excitation signals on the line 46 having increasingly higher frequencies. Once start-up is achieved, i.e., after two pulses of the initial excitation signal, if the phase of the feedback signal at the terminal 54B leads the signal at the terminal 54A the frequency of the output on the line 46 is increased, or vice versa.

Figure 2:
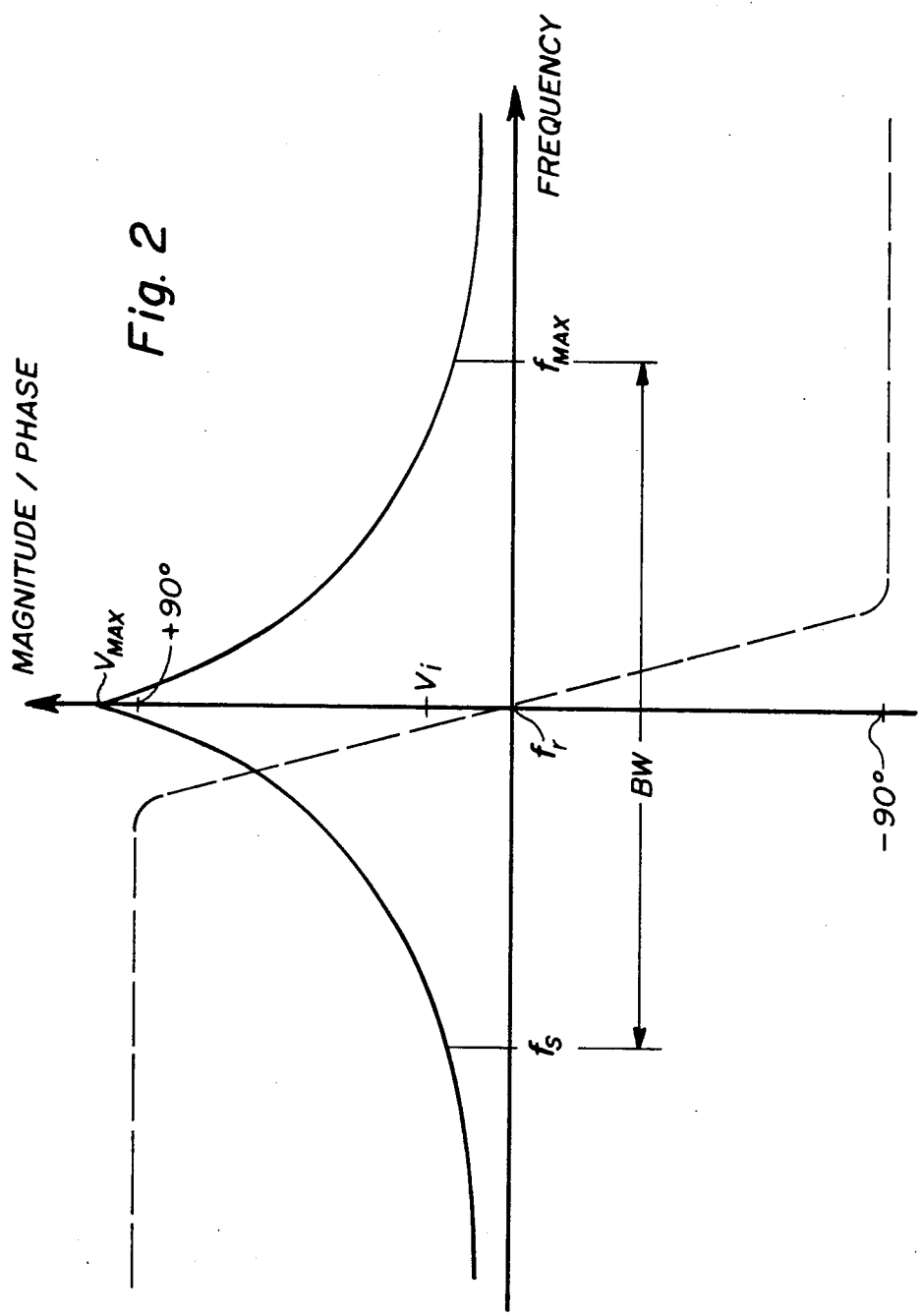
FIG. 2 is a graphical representation of the magnitude and the phase of a feedback signal measured with respect to an excitation signal both plotted as a function of the frequency of the excitation signal.

As seen with respect to FIG. 2 the magnitude of feedback signal representative of the oscillations of the probe 12 reach a maximum $V_{max}$ at the resonant frequency $f_r$ of the probe 12. In the present instance, assuming that the bridge 50 is balanced, the magnitude of the oscillation of the probe 12 as manifested by the magnitude of the electrical feedback signal falls away from the maximum as frequency is increased or decreased from the resonant frequency $f_r$. As also may be seen from FIG. 2 at the resonant frequency of the system the phase of the feedback signal shifts 180 degrees from a 90° leading posture at frequencies of excitation below the resonant frequency to 90° lagging above the resonant frequency. Once start-up is achieved the fact that the phase of the feedback signal leads that of the excitation signal (for $f_r$ greater than the frequency of the excitation signal) serves as a basis for the frequency search arrangement of the present invention.

The drive network 10 in accordance with the present invention includes a synchronous pulse generator network 64 which is coupled to the output of the oscillator 44 via a line 66 and also, via a line 68, to a suitable command source, such as a digital computer. The synchronous pulse generator 64 includes a clocked flip-flop 72 such as that sold by RCA as model number CD4013. The Q output of the flip-flop is connected to a threshold switch 74 comprising a diode 76 and a pair of resistors 78A and 78B. The point intermediate the resistors is connected over a line 82 to the inverting input of the level detector network 58 and thus serves as the voltage reference therefor. The Q-NOT output of the flip-flop 72 is applied over a line 84 to enable the amplifier 48. The same Q-NOT output is applied over a line 86 to a pulse generating network 88 comprising a diode 90 and a capacitor 92. The output of the pulse generating network 88 is applied over a line 94 to the noninverting input of the level detector network 58. It is noticed that upon enablement of the network 10, as manifested by the occurrence of the ENABLE signal on the line 68, the threshold voltage on the line 82 connected to the level detector network 58 is reduced to a voltage (typically zero volts) that is lower than the initial relatively high level $V_i$ present prior to enablement. As a result feedback signals of an amplitude lower than the value $V_i$ cause the amplifier 58 to respond. As will be noted this facilitates the definition of the frequency bandwidth to be searched.

In operation, a predetermined start frequency $f_s$ known to be below the resonant frequency $f_r$ of the probe 12 (see FIG. 2) is selected arbitrarily as the initial frequency of the excitation signal output of the oscillator 44 and a search bandwidth BW equal to $(f_{max}-f_s)$ is chosen. The search bandwidth BW includes the resonant frequency $f_r$. Typically, the resonant frequency $f_r$ of the probe 12 lies above the operating audio level (20 kHz) and below 100 kHz. If the probe is used, for example, to mix tabletted reagent a resonant frequency of approximately forty kHz is typical. As an example, for a probe 12 with a resonant frequency of 40 kHz the search bandwidth BW is five kHz.

Upon the receipt of an ENABLE command signal over the line 68 and at the next-occurring rising edge of the excitation signal applied over the line 66 the synchronous pulse generator 64 produces an output level change that is applied over the line 84 to enable the amplifier 48. This level change also produces an output pulse from the network 88 that is applied over the line 94 to the level detector network 58. The generation of the output pulse from the network 64 in a manner described guarantees that at start-up, from the perspective of the phase comparator 56, the feedback signal representative of the oscillation of the probe 12 applied over the line 60 thereto has a frequency greater than the frequency of the excitation signal applied thereto over the line 52. Accordingly, the phase comparator 56 serves to increase the output of the oscillator 44 progressively toward the resonant frequency of the system. In this manner the oscillator 44 is initially caused to output an increased excitation frequency. Once start-up is achieved in the manner described, so long as the phase of the signal on the line 60 leads the signal on the line 52, the frequency of the excitation signal on the line 46 is increased. This action continues until the resonant frequency of the system is encountered, at which time the phase difference between the signals on the lines 52 and 60 is zero.

Those skilled in the art having benefit of the teachings of the present invention may modify the same. These modifications lie within the scope of the invention defined by the claims.

What is claimed is:

1. In a drive network for an ultrasonic probe, the drive network being of the type having a source operative to generate probe excitation signals at any one of a predetermined plurality of selectable frequencies in a range of frequencies, means coupled to the probe and operative to generate an electrical feedback signal representative of the motion thereof, a phase comparator having a first input terminal connected to the excitation signal and a second input terminal connected to the feedback signal, the phase comparator being operative to control the frequency of the excitation signal generated by the source in a manner such that, at the start-up of the network, when the feedback signal has a frequency greater than that of the excitation signal the source is caused to apply to the probe an excitation signal at a predetermined higher frequency, wherein the improvement comprises:

a network responsive to a predetermined enable signal generated prior to the initial application to the probe of an excitation signal from the source at a first predetermined frequency for applying a pulse to the second input terminal of the phase comparator such that the frequency of the feedback signal applied to the phase comparator is greater than that of the excitation signal being applied to the phase comparator at the first input terminal thereof.

2. The network of claim 1 wherein the source provides a time varying excitation signal the amplitude of which is positive at predetermined periodic times, and wherein the network further comprises:

means responsive to the enable signal and to the excitation signal to generate the pulse at the start of the positive portion of the excitation signal next following the occurrence of the enable signal.

3. The network of claim 1 further comprising:

a level detector for comparing the magnitude of the feedback signal to a predetermined threshold; and means responsive to the enable signal to lower the theshold from a first value to a second, lower, value.

* * * * *